United States Patent [19]

Brooks

[11] Patent Number: 5,420,107
[45] Date of Patent: May 30, 1995

[54] METHOD AND COMPOSITION FOR ENERGY SOURCE SUPPLEMENTATION DURING EXERCISE AND RECOVERY

[76] Inventor: George A. Brooks, 2 Lost Valley Ct., Orinda, Calif. 94563

[21] Appl. No.: 279,829

[22] Filed: Jul. 25, 1994

Related U.S. Application Data

[63] Continuation of Ser. No. 471,287, Jan. 26, 1990, abandoned.

[51] Int. Cl.$^6$ .............. A61K 37/00; A61K 31/70; A61K 31/19; A61K 31/195
[52] U.S. Cl. ............................................. 514/2; 514/23; 514/557; 514/565
[58] Field of Search ................. 514/2, 23, 557, 565

[56] References Cited

U.S. PATENT DOCUMENTS

| | | | |
|---|---|---|---|
| 1,813,936 | 7/1931 | Kober | 514/578 |
| 4,604,286 | 8/1986 | Kawajiri | 424/601 |
| 4,871,550 | 10/1989 | Millman | 514/561 |

FOREIGN PATENT DOCUMENTS

182356 5/1986 European Pat. Off. .

OTHER PUBLICATIONS

Brooks, G. A., *Comparative Physiology and Biochemistry: Current Topics and Trends*, Vol. A, Circulation, Respiration, and Metabolism, R. Gilles (ed.), Springer Verlag, Heidelberg, (1985).
Brooks, G. A., Med. Sci. Sports Exerc. 18:360–368 (1986).
Brooks, G. A., Federation Proc. 45:2924–2929 (1986).
*Biochemical Aspects of Physical Exercise*, Brooks, G. A. et al. (eds.), Elsevier, Amsterdam, 1986.
Brooks, G. A. in *Exercies: Benefits, Limits and Adaptation*, Macleod, D. et al. (eds.), E. & F. N. Spon, London (1987).
Brooks, G. A. and C. M. Donovan, Am. J. Physiol. 244:E505–512 (1983).
Brooks, G. A. and D. A. Roth, Med. Sci. Sports Exerc. 21(2):s35–207 (1989).
Corsi, A. et al., Am. J. Physiol 223:219–222 (1972).
Davis, M. A. et al., Am. J. Physiol. 247(Endocrinol. Metab. 10):E362–E369 (1984).
Depocas, F. et al., Can. J. Physiol. Pharmacol. 47:603–610 (1969).
Deuticke, B. et al., Biochem. Biophys. Acta 507:137–155 (1978).
Dohm, G. L. et al., J. Appl. Physiol. 61(4):1353–1368 (1986).
Donovan, C. M. and G. A. Brooks, Am. J. Physiol. 244:E83–E92 (1983).
Fishbein, W. N., Science 234:1254–1256 (1986).
Foster, D. W., Diabetes 33:1188–1199 (1984).
Gaesser, G. A. and G. A. Brooks, Med. Sci. Sports Exerc. 16:29–43 (1984).
Gertz, E. W. et al., Circulation 63:1273–1279 (1981).
Gertz, E. W. et al., J. Clin. Invest. 82:2017–2025 (1988).
Gladden, L. B. and J. W. Yates, J. Appl. Physiol. 54: 1254–1260 (1983).

(List continued on next page.)

*Primary Examiner*—Raymond Henley, III
*Attorney, Agent, or Firm*—W. Patrick Bengtsson; Limbach & Limbach

[57] ABSTRACT

A supplement containing lactic acid salts and/or polymers, and optionally simple and/or complex carbohydrates, is employed to promote energy supply, fluid and electrolyte balance, blood glucose homeostasis, blood pH buffering and muscle as well as liver glycogen storage during and after strenuous exercise. The disclosed composition takes advantage of the presence of sodium-mediated intestinal lactate and glucose transporters, intestinal conversion of glucose to lactate, hepatic formation of glycogen from lactate, the preferential uptake of lactate for fuel by cardiac and red skeletal muscles, the alkalizing effect of the combustion of lactate to $CO_2$ and $H_2O$ and conversion to glucose of glycogen, and the presence of a sarcolemmal (muscle cell membrane) lactate/hydrogen ion (symport) transport protein to provide beneficial nutritional supplementation during exercise and subsequent recovery.

18 Claims, 5 Drawing Sheets

OTHER PUBLICATIONS

Granata, A. L. et al., Pflugers Archiv. 366:247–250 (1976).
Hildmann, B. et al., Biochem. J. 186:169–176 (1980).
Hughson, R. L. et al., J. Appl. Physiol. 62(5):1975–1981 (1987).
Hultman, E. H., Acta Physiol. Scand. 128(Suppl 556):75–82 (1986).
Johnson, J. A. and R. M. Fusaro, Advan. Metab. Disorders 6:1–55 (1972).
Jorfeldt, L., *Muscle Metabolism During Exercise*, Pernow, B. and B. Saltin (eds.), Plenum Press (1971).
Juel, C., Acta Physiol. Scand. 132:363–371 (1988).
Mazzeo, R. S. et al., Biomed. Mass. Spectrom. 9:310–314 (1982).
Mazzeo, R. S. et al., J. Appl. Physiol. 60:232–241 (1986).
Murray, R., Sports Med. 4:322–351 (1987).
Nadel, E. R. and S. R. Bussolari, American Scientist 76:350–360 (1988).
Newgard, C. B. et al., J. Biol. Chem. 258:8046–8052 (1983).
Newgard, C. B. et al., J. Biol. Chem. 259:6958–6963 (1984).
Roth, D. A. and G. A. Brooks, Med. Sci. Sports Exerc. 21(2)s35–206 (1989).
Smadja, C. et al., Am. J. Physiol. 254(Endocrinol. Metab. 17):E407–E413 (1988).
Stanley, W. C. et al., Am. J. Physiol. 249:E595–E602 (1985).
Stanley, W. C. et al., J. Appl. Physiol. 60:1116–1120 (1986).
Stanley, W. C. et al., Metabolism 37:850–858 (1988).
Storelli, C. et al. Pflugers Arch. 388:11–16 (1980).
Wasserman, D. H. et al., J. Appl. Physiol. 63:2411–2417 (1987).
Watt, P. W. et al., Biochem. Biophys. Acta 944:213–222 (1988).
Wilson, T. H., J. Biol. Chem. 222: 751–763 (1956).

METHOD AND COMPOSITION FOR ENERGY SOURCE SUPPLEMENTATION DURING EXERCISE AND RECOVERY

This is a continuation of applicaiton Ser. No. 07/471,287, filed on Jan. 26, 1990, now abandoned.

TECHNICAL FIELD

This invention relates generally to nutritional supplements, and, in particular, to a novel method and composition beneficial to a mammal's fluid, electrolyte and carbohydrate balance during exercise and subsequent recovery.

BACKGROUND OF THE INVENTION

Recent advances in basic biochemistry and exercise physiology have shown that the formation and removal of lactic acid is an integral part of both digestive and metabolic processes.

According to the 'Glucose Paradox' hypothesis of McGarry (as reviewed by Foster, D., Diabetes 33:1188–1199 (1984); also see Newgard, C. B. et al., J. Biol. Chem. 258:8046–8052 (1983)), dietary carbohydrate courses an indirect route before becoming liver glycogen. It is known that dietary carbohydrate is digested and then enters the portal circulation (i.e., the vein between the small intestine and the liver) largely as glucose.

In contrast to traditional theories which hold that the liver extracts large amounts of portal blood glucose for synthesis of glycogen, it is now believed that portal glucose bypasses the liver and enters the systemic circulation through the hepatic vein. Much of this glucose then reaches the resting musculature, where it is either stored as glycogen or converted to lactic acid. This lactic acid then either diffuses or is transported from the sites of production and reaches the systemic circulation. Much of the circulating lactic acid is removed by the liver.

In the glycogen-depleted liver, lactic acid becomes the preferred precursor material from which to synthesize glycogen. Because glycogen is paradoxically synthesized by a rather circuitous pathway, the process is alternatively termed the Glucose Paradox, or the Indirect Glucose to Liver Glycogen Pathway (FIG. 1).

According to the 'Lactate Shuttle' hypothesis of Brooks (*Comparative Physiology and Biochemistry: Current Topics and Trends, Volume A, Respiration-Metabolism-Circulation*, R. Gilles (ed.), Springer Verlag, Heidelberg, (1985); Brooks, G. A., Med. Sci. Sports Exerc. 18:360–368 (1986); Brooks, G. A., Federation Proc. 5:2924–2929 (1986); *Biochemical Aspects of Physical Exercise*, Brooks, G. A. et al. (eds.), Elsevier, Amsterdam, 1986); *Exercise, Limits and Adaptation*, Brooks, G. A. et al. (eds.), E. & F. N. Spon, London (1987)), lactic acid is an important fuel source for exercise as well as resting and exercise-recovery conditions (FIG. 2). During exercise, active fast-twitch muscles produce lactic acid, which is then available as a fuel for slow-twitch, highly oxidative skeletal muscle fibers (Donovan, C. M. and G. A. Brooks, Am. J. Physiol. 244:E83–E92 (1983); Brooks, G. A. and C. M. Donovan, Am. J. Physiol. 244:E505–512 (1983); Corsi, A. et al., Am. J. Physiol 223:219–222 (1972); Granata, A. L. et al., Pflugers Archiv. 366:247–250 (1976); Jorfeldt, L., Acta Physiol. Scand. Suppl. 338:1–67 (1971); Mazzeo, R. S. et al., Biomed. Mass. Spectrom. 9:310–314 (1982); Mazzeo, R. S. et al., J. Appl. Physiol. 60:232–241 (1986); Stanley, W. C. et al., Am. J. Physiol. 249:E595–602 (1985); Stanley, W. C. et al., J. Appl. Physiol. 60:1116–1120 (1986)) and heart tissue (Gertz, E. W. et al., Circulation .63:1273–1279 (1981)).

The oxidation of lactic acid during exercise can be appreciated on both relative and absolute bases. Of the lactic acid produced and removed during exercise, approximately 75% is removed by oxidation, and 20% is converted to glucose (Depocas, F. et al., Can. J. Physiol. Pharmacol. 47:603–610 (1969); Donovan, C. M. and G. A. Brooks, Am. J. Physiol. 244:E83–E92 (1983); Stanley, W. C. et al., Metabolism 37:850–858 (1988)). Of this latter portion, most will ultimately be oxidized also (Brooks, G. A. and C. M. Donovan, Am. J. Physiol. 244:E505–512 (1983)). Quantitatively, lactic acid oxidation exceeds glucose oxidation during exercise, with 10 to 25% of the total energy supplied derived from lactic acid oxidation. These findings suggest that it may be desirable to employ lactic acid as a supplement during and/or after exercise.

However, the use of lactic acid as a fuel in the body carries with it potential penalties. Lactic acid accumulation in the muscle is painful and interferes with contraction processes. Further, large amounts of lactic acid in the blood cause pH to fall which is physically and psychologically distressing to the performer. These disadvantages are associated with the hydrogen ion ($H^\oplus$, or proton) which results when lactic acid dissociates in aqueous solutions. For these reasons, lactic acid accumulation has long been suspected as a cause of muscle fatigue (Brooks, G. A. and T. D. Fahey, *Exercise Physiology: Human Bioenergetics and its Applications*, Chapter 32, Macmillan, New York, 1984).

Therefore, it may be advantageous to provide glycogen depleted subjects with a 'lactic acid-like' material to aid in restoration of liver glycogen as well as to restore blood glucose and muscle glycogen.

Furthermore, in comparison to providing dietary glucose to an individual engaged in prolonged, strenuous exercise, it would be more advantageous to provide a 'lactic acid-like' substance which would provide a more immediate fuel source.

Thus, on the bases of both the 'Glucose Paradox' and 'Lactate Shuttle' concepts, providing a 'lactic acid-like' material to athletes during exercise and recovery from exercise would also augment the beneficial effects of providing dietary glucose.

Disclosure of the Invention

In accordance with the present invention, a novel method and composition beneficial to a mammal's fluid, electrolyte and carbohydrate balance during exercise and subsequent recovery are provided.

In one aspect, the invention provides a method of supplying nutritional supplementation to mammals comprising providing an aqueous solution of at least one lactic acid salt. This solution is administered in oral dosage form to a mammalian host in an amount sufficient to affect the mammal's fluid, electrolyte or carbohydrate balance during exercise and/or subsequent recovery.

In another aspect, a nutritional supplement is provided comprising an aqueous solution of at least one organic lactic acid salt in an amount sufficient to affect a mammal's fluid, electrolyte or carbohydrate balance during exercise and/or subsequent recovery.

In other aspects, the present nutritional supplement includes mixtures of organic and inorganic lactic acid salts, lactate polymers, and/or simple and complex carbohydrates.

DETAILED DESCRIPTION OF THE INVENTION

Figure 1:
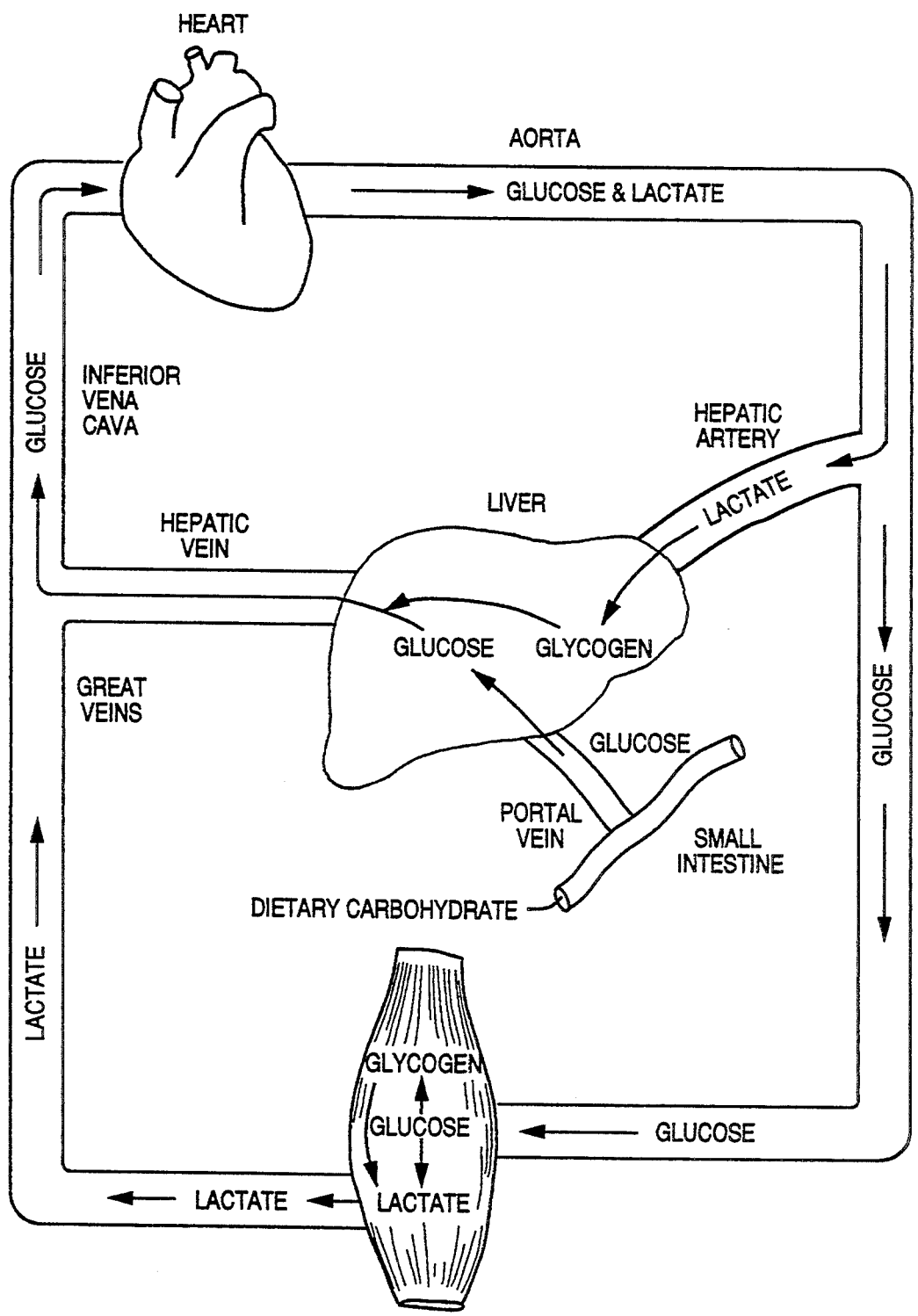
FIG. 1 is a diagrammatic representation of the 'Glucose Paradox' hypothesis and depicts the conversion of dietary carbohydrate to liver glycogen via the indirect pathway.
Figure 2:
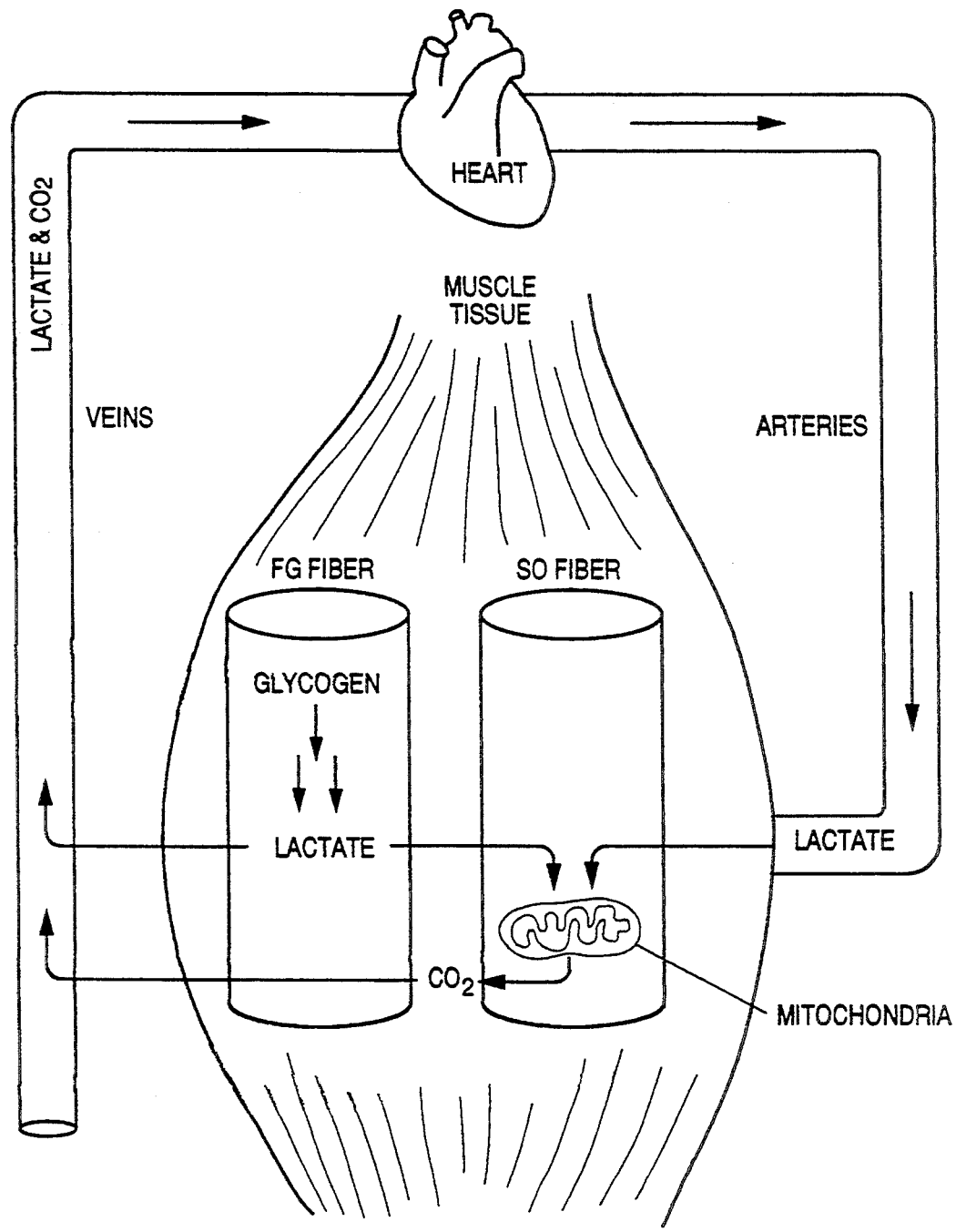
FIG. 2 is a diagrammatic representation of the biochemical pathway known as the 'Lactate Shuttle,' by which lactate formed in some tissues, such as contracting white skeletal muscle (FG, fast glycolytic) fibers, provides an energy source for other tissues such as contracting red skeletal muscle (SO, slow oxidative) fibers and heart.

In accordance with the present invention, a novel method and composition beneficial to a mammal's fluid, electrolyte and carbohydrate balance during exercise and subsequent recovery are provided.

It is believed that lactic acid becomes the preferred precursor material from which to synthesize glycogen in the glycogen depleted liver. In addition, according to the 'Lactate Shuttle' hypothesis, lactic acid is an important fuel source for exercise as well as resting and exercise recovery conditions. Therefore, it is considered advantageous to provide glycogen-depleted subjects with some form of a lactic acid supplement to aid in restoration of liver glycogen, as well as a material to restore blood glucose and muscle glycogen.

However, as the use of lactic acid as a fuel in the body is not particularly desirable, it would be more advantageous to provide a 'lactic acid-like' substance which would provide a more immediate fuel source. Furthermore, on the basis of both the 'Glucose Paradox' and 'Lactate Shuttle' concepts, providing a 'lactate-like' material to athletes during exercise and recovery from exercise would augment the beneficial effects of providing dietary glucose or other carbohydrates.

In order to alleviate the problems inherent in using lactic acid as a dietary supplement, it is considered desirable to substitute an organic cation for the $H^{\oplus}$ of lactic acid to yield alkalizing effects. Because lactate is combusted as an acid ($C_3H_6O_3$), not an anion ($C_3H_5O_3$), the combustion of an externally supplied salt of lactic acid (Equation 1) effects the removal of the proton taken up during endogenous lactic acid production (Gladden, L. B. and J. W. Yates, J. Appl. Physiol. 54:1254–1260 (1983)).

$$CHO^3H^5O_3^{\ominus} + H^{\oplus} + 3O_2 \rightarrow 3H_2O + 3CO_2 \qquad (Eq.\ 1)$$

A side benefit of alkalizing the plasma by feeding lactate would be to enhance movement (efflux) of lactic acid from active muscles into plasma, a process which is inhibited by low (relative to muscle) blood pH (Brooks, G. A. and D. A. Roth, Med. Sci. Sports Exerc. 21(2):S35-207 (1989); Roth, D. A. and G. A. Brooks, Med. Sci. Sports Exerc. 21(2):S35-206 (1989)). Moreover, maintenance of a more normal blood pH during strenuous exercise would decrease the performer's perceived level of exertion.

The conversion of lactate to glucose in the liver and kidneys also has alkalizing effects by removing two protons for each glucose molecule formed (Equation 2).

$$2C_3H_5O_3 + 2H^{\oplus} \rightarrow C_6H_{12}O_6$$

Thus, whether by oxidation or conversion to glucose, clearance of exogenously supplied lactate lowers the body concentration of $H^{\oplus}$, raising pH.

In addition, caloric replacement during exercise is limited by a variety of factors mainly related to gastric emptying. Concentrated and acidic solutions slow emptying and further result in contraction and acidification of blood plasma volume (Murray, R., Sports Medicine 4:322–351 (1987)). Conversely, alkaline salts speed gastric emptying. Thus, it would not be feasible to administer lactic acid as a nutritional supplement, as it is not only extremely unpalatable, but also counterproductive.

Further, by their natures, particular salts either speed or inhibit gastric emptying, or act as intestinal irritants. Therefore, a lactic acid supplement in accordance with the invention will contain a pH neutral, non-irritating salt of lactic acid to speed gastric emptying.

There are other phenomena of exercise physiology which make a 'lactate-like' supplement desirable either alone or in combination with other nutritional components. For example, intestinal transporters of both glucose (Murray, R., Sports Medicine 4:322–351 (1987); Nadel, E. R. and S. R. Bussolari, American Scientist 76:350–360 (1988)) and lactate (Hildman, B. et al., Biochem. J. 186:169–176 (1980); Storelli, C. et al. Pflugers Arch. 388:11–16 (1980)) depend on co-transport with sodium ion. Therefore, dilute sodium solutions promote entry of essential metabolites into the portal and systemic circulations from the intestinal lumen.

Inclusion of sodium ion in a 'lactic acid-like' supplement is important for other reasons. During prolonged exercise, significant sodium losses occur in sweat. This loss of sodium leads to a contraction of plasma volume and a suppression of the thirst mechanism. Moreover, resorption of water in distal renal tubules is sodium dependent. Therefore, stimulation of the sodium-dependent dispogenic drive will stimulate thirst, maintain plasma volume, and minimize urine production (Brooks, G. A. and T. D. Fahey, Exercise Physiology: Human Bioenergetics and its Applications, Chapter 32, Macmillan, New York, 1984; Brooks, G. A. and T. D. Fahey, Fundamentals of Human Performance, Macmillan, New York, 1986; Nadel, E. R. and S. R. Bussolari, American Scientist 76:350–360 (1988)).

A result reported long ago (Wilson, H., J. Biol. Chem. 222:751–763 (1956)), and recently confirmed (Smadja, C. et al., Am. J. Physiol. 254(Endocrinol. Metab. 17):E407–E413 (1988)), is that cells of the intestinal wall convert dietary glucose to lactate. Previously, without the conceptual framework of the Lactate Shuttle and Glucose Paradox, this result was generally overlooked, disregarded, or classified as an anomaly. However, by converting some of a dietary carbohydrate load, the intestine provides a precursor for glycogen synthesis to the liver as well as releasing into the circulation an oxidizable fuel which does not elicit an insulin response.

It is now apparent that under appropriate circumstances the liver produces lactate as part of a coordinated physiological response. For example, it has been shown that after a mixed meal, the liver releases lactate (Davis, M. A. et al., Am. J. Physiol. 247(Endocrinol. Metab. 10):E362–E369 (1984)). Extrahepatic tissues clear this lactate and maintain the arterial lactate concentration below that of the hepatic vein.

More recently, it was demonstrated that following the onset of exercise, liver releases lactate (Wasserman, D. H. et al., J. Appl. Physiol. 63:2411–2417 (1987)). Again, because the arterial lactate level is maintained below that in the hepatic vein, the results indicate that skeletal muscle and other extrahepatic sites are of major importance in clearing blood lactate.

Another overlooked finding is that epidermal cells take up glucose and release significant quantities of lactate, despite apparently adequately oxygen supply. In their review of 1972, Johnson and Fusaro made some remarkable attempts to interpret this and related findings concerning carbohydrate metabolism in the skin (Johnson, J. A. and R. M. Fusaro, Advances in Metabolic Disorders 6:1–55 (1972). Again, as noted above, with the conceptual framework of the Lactate Shuttle and Glucose Paradox it is possible to recognize that the skin assists in the coordination of metabolic functions among and between tissues. Supplying an exogenous, non-acidic form of lactate (i.e., a 'lactic acid-like' supplement) would therefore assist the function of the skin and other lactate producing tissues.

Since the late 1970's it has been known that erythrocytes contain a membrane transport protein for the exchange of lactate (Deuticke, B. et al., Biochem. Biophys. Acta 507:137–155 (1978)). Recently, investigators have studied isolated skeletal muscles and have obtained results which support the presence of a muscle lactate transporter (Jeul, C., Acta Physiol. Scand. 132:363–371 (1988); Watt, P. W. et al., Biochem. Biophys. Acta 944:213–222 (1988)).

Most recently, Brooks and Roth (Brooks, G. A. and D. A. Roth, Med. Sci. Sports Exerc. 21(2) (1989)) and Roth and Brooks (Roth, D. A. and G. A. Brooks, Med. Sci. Sports Exerc. 21(2) (1989)), using muscle membrane preparations, have demonstrated that the presence of a lactate transporter is an essential constituent of the Lactate Shuttle hypothesis and explains the basis of a recently described muscle myopathy (Fishbein, W. N., Science 234:1254–1256 (1986)). This presents another important reason why a non-acidic form of lactate would be expected to promote muscle cell function.

In diabetes, cellular uptake of glucose is limited by lack of insulin (Type I), or resistance to insulin (Type II). Moreover, because glycolysis can not proceed to lactate production without cellular glucose uptake, diabetics possess reduced capacity to utilize bloodborne glucose as fuel. However, provision of an exogenous lactic acid supplement such as the nutritional supplement of the present invention to diabetics could represent a novel and potentially effective means to bypass the diabetic limitation of cellular glucose uptake required for lactic acid production. Moreover, the alkalizing effects of metabolizing such a lactic acid supplement could help to offset diabetic ketoacidosis.

Modes of Practicing the Invention

The novel method provided in accordance with the present invention comprises the administration of an aqueous solution of at least one lactic acid salt in an amount sufficient to affect a mammal's fluid, electrolyte or carbohydrate balance during exercise and/or subsequent recovery.

The present nutritional supplement comprises an aqueous solution of at least one organic lactic acid salt in an amount sufficient to affect a mammal's fluid, electrolyte or carbohydrate balance during exercise and/or subsequent recovery.

In other aspects, the present nutritional supplement includes mixtures of organic and inorganic lactic acid salts, lactate polymers, and/or simple and complex carbohydrates.

An inorganic lactic acid salt will be generally in accordance with the following formula:

where the L-form of the lactate ion is depicted.

In a presently preferred embodiment, the inorganic lactic acid salt is sodium lactate, so as to provide sodium as well as lactate ions in the nutritional supplement. The sodium lactate concentration in the present supplement will generally range up to approximately 0.2%. Desirably, the sodium content will be sufficient to compensate for sodium losses in sweat (18 mEq/liter being representative of the sodium content of sweat in trained individuals). Further, the sodium content in the preferred nutritional supplement will provide the sodium-dependent dispogenic drive, thereby minimizing urine production and stimulating the thirst mechanism.

However, it will be recognized that the sodium ion in the inorganic lactic acid salt could be substituted in whole or in part by, e.g., calcium, potassium, ammonium, magnesium, etc., as well as other inorganic cations, while generally maintaining the benefits of the present invention.

An organic lactic acid salt will be generally in accordance with the following formula:

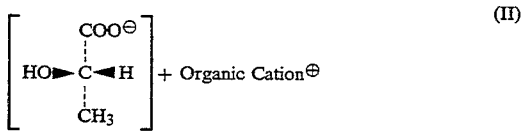

where the L-form of the lactate ion is depicted.

In a presently preferred embodiment, the organic lactic acid salt is employed as a salt or lactate polymer with an amino acid as a base.

In selecting amino acid residues to form organic salts and lactate polymers in accordance with the present invention, the residues can be generally subclassified into four major subclasses as follows:

Acidic, i.e., the residue has a negative charge due to loss of H⊕ ion at physiological pH;

Basic, i.e., the residue has a positive charge due to association with H⊕ ion at physiological pH;

Neutral/non-polar, i.e., the residues are not charged at physiological pH and the residue is repelled by aqueous solution; and Neutral/polar, i.e., the residues are not charged at physiological pH and the residue is attracted by aqueous solution.

It is understood, of course, that in a statistical collection of individual residue molecules some molecules will be charged, and some not. To fit the definition of charged, a significant percentage (at least approximately 25%) of the individual molecules are charged at physiological pH.

For the naturally occurring protein amino acids, subclassification according to the foregoing scheme is as follows:

Acidic: Aspartic acid and Glutamic acid;
Basic: Arginine, Histidine and Lysine;
Neutral/polar: Glycine, Serine, Threonine, Tyrosine, Asparagine, Glutamine and Cysteine;
Neutral/non-polar: Alanine, Valine, Isoleucine, Leucine, Methionine, Phenylalanine and Tryptophan.

In the present application, the L-form of any amino acid residue having an optical isomer is intended unless otherwise expressly indicated.

An acid-base reaction involving lactic acid (L(+)-lactic acid) and L-isomeric forms of basic amino acids such as arginine, histidine and lysine will form organic lactic acid salts or lactate polymers useful in the invention.

Such organic lactic acid salts will generally be in accordance with the following formula:

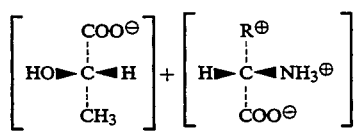

(III)

wherein R⊕ is a substituent group with a net positive charge at physiological pH.

The organic lactic acid salts and lactate polymers useful in the practice of the invention are readily formed by acid-base reaction. For example, in a presently preferred embodiment, L(+)-lactic acid and L-basic amino acid are combined in solution under conditions which permit the formation of poly(base+lactic acid) to form a lactate polymer.

In one preferred embodiment, L(+)-lactic acid and L-arginine are combined in solution to provide the desired organic lactic acid salt or lactate polymer. Depending upon the reaction conditions, such as solution pH, order of addition of reactants, and the like, the L-arginyl-L(+)-lactic acid will form monomers, dimers, trimers and/or polymers of the amino and/or guanidinyl forms, generally in accordance with the following structure:

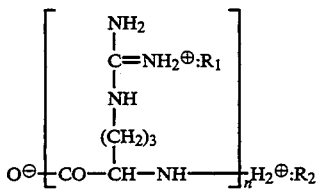

(IV)

where n is a whole number ≧ 1; and each R can independently be

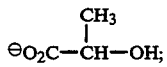

provided that when n=1, at least one of $R_1$ and $R_2$ must be lactate anion.

It will be understood that when n is greater than 1 in formula IV, a certain number of the positions indicated by $R_1$ groups may not be lactate anions, a circumstance that can be likened to an "unsaturated" polymer. However, so long as a sufficient number of lactate anions are bound to the polymer so as to provide the recited benefits, such embodiments are considered to be within the scope of the invention.

As an example of such preferred embodiments, the L-arginyl-l(+)-lactate can be formed by adding an equimolar amount of L-arginine to a solution of L-(+)-lactic acid adjusted to basic pH. The major species of the preferred lactate polymer so prepared will have the following general structure:

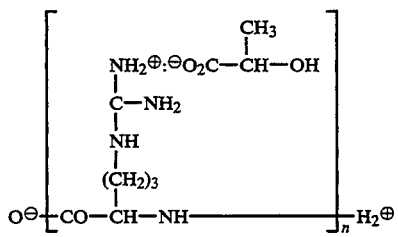

(V)

where n is a whole number ≧ 1.

In the acid environment of the stomach, this polymer compound will readily dissociate to free lactate, lactic acid and free arginine (or other amino acids). In this case, lactic acid formation will actually scavenge hydrogen ion and lower pH.

It will be apparent that other organic cations and neutral amino acids can be employed in place of basic amino acids to form the organic lactic acid salts and lactate polymers of the present invention. For example, other basic amino acids could be utilized as partial or total substitutes for the arginine in the lactate polymer to form lactate copolymers or polymers useful in the practice of the present invention. Thus, the term lactate polymer will be understood to include all such polymers and copolymers of lactic acid.

A dosage of organic lactic acid salt or lactate polymer in the nutritional supplement of the invention will usually raise the total lactate ion content to less than approximately 9.8% while limiting the total sodium and heavy metal ion content supplied as inorganic lactate to less than approximately 0.2%.

In a presently preferred embodiment, the present supplement will include approximately 1.8% organic lactate polymer and 0.2% sodium lactate, so that the total lactate content will approximate 2%.

In contrast to the liver, which synthesizes most glycogen from lactate via the indirect pathway, skeletal muscle synthesizes glycogen almost exclusively from blood glucose. Because the primary physiological priorities after exhausting exercise are to restore blood glucose, and heart and muscle glycogen before restoring liver glycogen (Gaesser, G. A. and G. A. Brooks, Med. Sci. Sports Exerc. 16:29–43 (1984)), the nutritional supplement of the present invention will preferably include an addition of simple and/or complex carbohydrates to meet all of the physiological priorities.

Representative simple carbohydrates include monosaccharides, such as glucose, fructose, mannose and galactose, which are readily incorporated into the host's metabolic pathways. The preferred simple carbohydrates are glucose and fructose.

Representative complex carbohydrates include disaccharides, such as sucrose, maltose and lactose, and polysaccharides, such as glucose polymers and copolymers, most usually of from five to ten monomeric units, which are incorporated into the host's metabolic pathways only after reduction to simple carbohydrates by, e. g., digestion, hydrolysis and various of the host's catabolic pathways. The terms glucose polymer and poly glucose are used in a general sense to mean complex carbohydrates which contain glucose monomers. Presently preferred glucose polymers include dextrins, intermediate in complexity between starch and maltose. Dextrins are generally obtained by hydrolysis of starch and are available commercially from numerous sources.

In a presently preferred embodiment, the present supplement will include, as a simple carbohydrate, approximately 2% glucose in order to provide ready support of blood glucose level. In this way, metabolism in glucose-dependent cells is supported as is muscle glycogen restitution during recovery. Alternatively, fructose can be used as a supplement to or replacement for glucose to provide similar benefits in the supplement.

In addition, the supplement will desirably contain at least one complex carbohydrate, such as a glucose polymer, to provide carbohydrate energy in a form to minimize osmotic pressure, thereby maximizing gastric emptying and intestinal absorption. In certain embodiments, the present supplement will contain approximately four percent glucose polymer to provide the desired carbohydrate energy source.

Various alternative embodiments of the invention will also supply lactate in the form of co-polymers and/or aggregates of polysaccharides formed, for example, by exposing these materials to concentrated solutions of L-(+)-lactic acid.

It must be realized at this point that, with possible exception of the sodium lactate component which should not be increased beyond the stated ranges, it is possible to adjust the proportions of the above stated components of the present supplement across a broad concentration range.

For example, it is possible to substitute calcium, potassium, ammonium and/or magnesium lactate for sodium lactate. The preferred substitutions will be for minor amounts of sodium ion as follows:

5 meq ($K^{\oplus}$), 2 meq ($Ca^{\oplus\oplus}$), 1 meq ($Mg^{\oplus\oplus}$), and <1 meq ($NH_4^{\oplus}$).

Similarly, depending on palatability, the lactate polymer component of the supplement can be increased (to 100% of the organic material) provided the total solute concentration in the supplement as administered orally is less than approximately 10%.

In various embodiments, the content of the lactate polymer component of the present nutritional supplement can be increased and the sodium lactate component eliminated to provide a sodium-free version of the present nutritional supplement.

Additionally, it may also be considered desirable in certain embodiments to include approximately 0.5 to 2.0% fructose by reducing the glucose and poly glucose contents of the preferred supplement. Inclusion of fructose would assist in liver glycogen restitution after exercise. More importantly, a small amount of fructose could enhance (sweeten) the taste of the present supplement.

Dilutions of any and all components are also possible. As noted above, dilution of the product might be desirable depending on user preference and specific application. Also, it is realized that the above stated concentrations apply only to dilution with distilled water. Alternatively, users may prefer tap water which will vary in mineral content. If tap water is used, 100 gram quantities of the present nutritional supplement should be diluted to 1.05 liters to account for the approximate concentration of dissolved minerals in tap water.

Inclusion of small amounts of ammonium lactate (0.025–0.05 mM) can also be desirable to help control pH and color stability of the supplement, as tap water is known to vary in pH and salt content. This basic form of lactate (i.e., ammonium lactate) could also assist in buffering of endogenous lactic acid during very strenuous exercise.

In accordance with the method of the present invention, an aqueous solution of inorganic or organic lactic acid salts or a mixture thereof in an amount sufficient to affect a host mammal's fluid, electrolyte or carbohydrate balance is administered to the host during exercise and/or subsequent recovery.

To this end, the present invention provides supplements containing an effective amount of the described lactic acid salts, which can, alone, serve to provide the above-recited therapeutic benefits. Such compositions can also be provided together with physiologically tolerable liquid, gel or solid diluents, adjuvants and excipients.

These supplements can be administered to mammals for veterinary use, such as with domestic animals, and clinical use in humans in a manner similar to other therapeutic agents. In general, the dosage required for therapeutic efficacy will range from about 0.1 to 50%, more usually 1 to 10% by weight. Alternatively, dosages within these ranges can be administered by constant infusion over an extended period of time, not usually exceeding 24 hours, until the desired therapeutic benefits have been obtained.

Typically, such supplements are prepared as oral formulations for conventional oral administration. Oral formulations can include such normally employed excipients as, for example, pharmaceutical grades of mannitol, lactose, starch, magnesium stearate, sodium saccharin, cellulose, magnesium carbonate, silicon dioxide and the like. These compositions take the form of solutions, suspensions, tablets, pills, capsules, sustained release formulations, or powders, and contain 1%–50%, preferably 5%–10%, of active ingredient.

In addition, if desired the supplement may contain minor amounts of auxiliary substances such as wetting or emulsifying agents to enhance solubility, stabilizing or pH buffering or indicating agents, and the like.

For certain applications, the supplement could also be administered, e.g., parenterally, by injection or intravenous drip. Additional formulations which are suitable for other modes of administration include suppositories and intranasal aerosols. For suppositories, traditional binders and excipients may include, for example, polyalkylene glycols or triglycerides; such suppositories may be formed from mixtures containing the active ingredient in the range of 0.5% to 10% preferably 1%–2%.

During sustained exercise, the dosage or consumption of the present nutritional supplement will desirably balance the fluid and energy losses experienced during exercise, most usually up to a rate of approximately 250 ml/15 min (1 liter/hr) of 10% solution in a human host. For maximal gastric emptying, the supplement solution concentration will desirably be limited to approximately 10% (w/v) (Murray, R., Sports Medicine 4:322–351 (1987)).

For strenuous, but intermittent, physical exercise, where caloric replacement is a higher priority than fluid replacement (e.g. in body building and similar forms of muscular exercise) the dosage concentration will preferably range from approximately 15 to 25%.

During recovery from strenuous exercise, the dosage of the present nutritional supplement will desirably be administered immediately after exercise, most usually as a 10% solution. The present nutritional supplement can also be consumed as a beverage with foods, or in concentrated form (up to approximately 50% (w/v) solution) as a meal substitute.

In various clinical applications of the present invention, such as nutritional supplements for diabetic hosts to provide an exogenous lactic acid supplement to bypass the diabetic limitation of cellular glucose uptake and to offset diabetic ketoacidosis, the mode of administration and the appropriate formulation will routinely be determined to accommodate the particularized requirements of each individual host.

The unique features of the presently preferred nutritional supplement include:

(1) Salts of lactic acid are used to maximize oxidizable carbohydrate energy delivery during exercise, to buffer endogenous lactic acid, and to support liver glycogen resynthesis during recovery;

(2) Relatively high sodium content is provided to stimulate thirst, thereby supporting maintenance of plasma and body fluid volume, as well as intestinal lactate and glucose uptakes;

(3) Carbohydrate is also provided in traditional forms (free fructose and glucose, as well as poly glucose). In this way, the maximal concentration of carbohydrate energy is provided in the present nutritional supplement; and (4) A small amount of organic, pH sensitive food coloring can be added to assist in adjusting concentration of the solution. In this way, users of the supplement could adjust the concentration from approximately 2–10% by comparing the beverage color with a color code, e.g., printed on the package.

The present invention will be further described by reference to the following examples.

Experimental

The following examples serve to illustrate certain preferred embodiments and aspects of the present invention and are not to be construed as limiting the scope thereof.

In the disclosure which follows, weights are given as moles (mol), grams (g) or milligrams (mg), concentrations are given as molar (M), millimolar (mM) or percent by weight in 100 milliliters volume (%) and volumes are given as liters (l) or milliliters (ml), unless otherwise indicated.

EXAMPLE 1

A lactate polymer in accordance with the invention was formed by acid-base reaction as follows:

Ninety grams of L(+)-lactic acid was dissolved in 1l of distilled $H_2O$ to form a 1M solution. The pH of this solution was adjusted to 9.2 using NaOH at 70° C. To this solution 1 mol (174 g) of L-arginine was added, while maintaining basic pH with further additions of NaOH.

The mixture was evaporated at 90° C. to approximately 50% of the original volume (elapsed time of one day). To this concentrated mixture 10 g of $SiO_2$ was added as a drying and anticaking agent. The mixture was spread evenly on a tray and dried by evaporation at 90° C. (elapsed time of two days). This provided a polyarginyl lactate polymer to be administered, together with optional amendments of simple and complex carbohydrates, flavorings, and the like, in the nutritional supplements of the present invention.

EXAMPLE 2

Five trained, fasted male cyclists volunteered as subjects and each rode a cycle ergometer (Monark Co.) three different times at 50% of the subject's determined $V_{O_2}max$ for 180 minutes.

Using a double-blind procedure, with balanced order of administration, subjects were fed either solution PL (a 7% solution of 80% lactate polymer/20% sodium lactate in water), solution GP (a 7% solution of multidextrin in water) or solution C (a placebo of water sweetened with Aspartame ®) five minutes before exercise and at 20 minute intervals during exercise.

Veneous blood samples were collected from each subject at rest and at 20 minute intervals during exercise to measure blood glucose, pH and bicarbonate ($HCO_3$). Oxygen consumption, electrocardiagram, blood pressure, ventilation and perceived exertion (using the scale of Borg, G., In: *Frontiers of Fitness*, Shephard, R. J. ed., Charles C. Thomas, Springfield, Ill. pp. 287 et seq. (1971)) were monitored every 20 minutes during exercise. Rectal temperature ($T_r$) and skin temperature of the back ($T_{sb}$) and chest ($T_{sc}$) were monitored continuously.

The results were as indicated in Table I and in the Figures.

TABLE I

Measurement of Venous Blood pH, $HCO_3$ and Glucose After 180 Minutes of Exercise at 50% $V_{O_2}max$

| Soln | pH | bicarbonate (mM) | glucose conc. (mM) | glucose decrease from rest |
|---|---|---|---|---|
| C | 7.38 ± 0.03 | 26.2 ± 1.0 | 3.41 ± 0.3 | 1.14 ± 0.2 |
| GP | 7.43 ± 0.01 | 26.7 ± 1.0 | 3.93 ± 0.4 | 0.42 ± 0.3 |
| PL | 7.47 ± 0.01 | 30.6 ± 0.9 | 4.04 ± 0.1 | 0.24 ± 0.1 |

Figure 4:
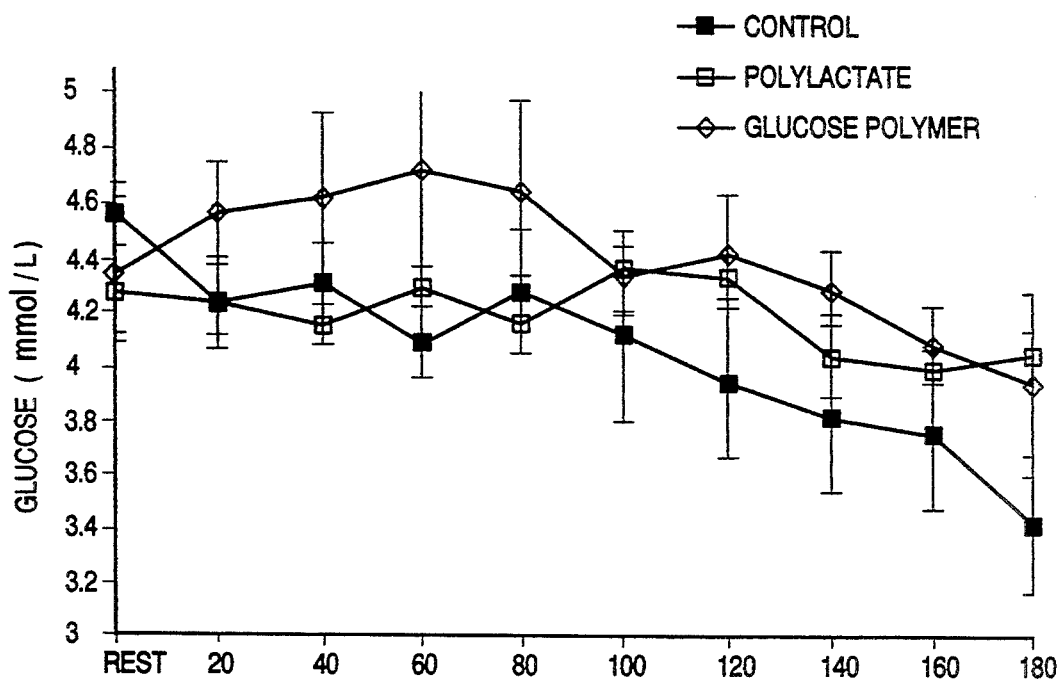
FIG. 4 is a graphic comparison of the venous blood glucose of subjects receiving a supplement according to the invention with subjects receiving carbohydrate or water during sustained exercise.
Figure 5:
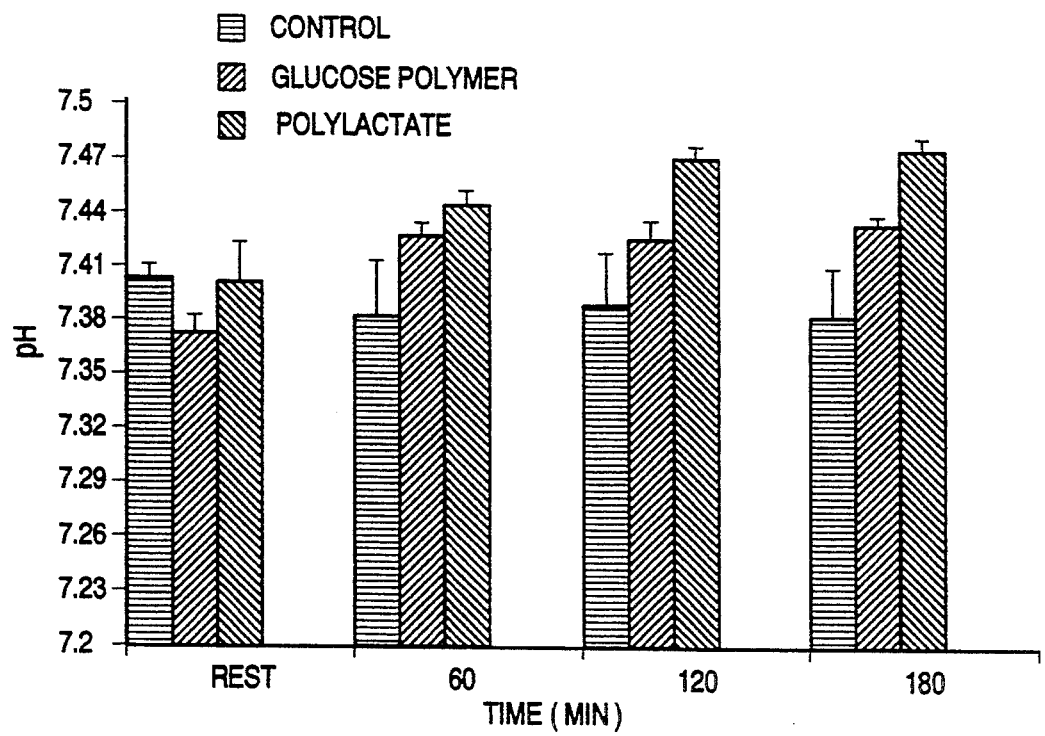
FIG. 5 is a graphic comparison of the venous blood pH of subjects receiving a supplement according to the invention with subjects receiving carbohydrate or water during sustained exercise.
Figure 6:
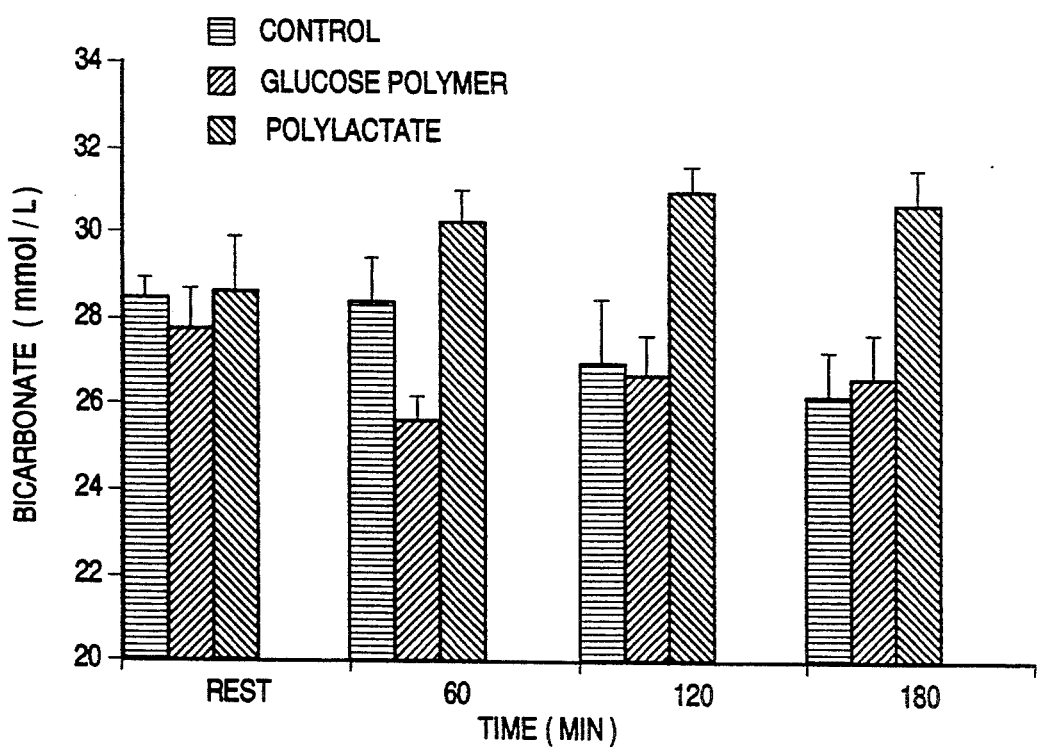
FIG. 6 is a graphic comparison of the venous blood bicarbonate of subjects receiving a supplement according to the invention with subjects receiving carbohydrate or water during sustained exercise.

As can be seen from Table I and FIGS. 4 to 6, after 180 minutes of exercise, blood glucose, blood pH and blood bicarbonate levels were higher for subjects receiving a supplement in accordance with the present invention, compared to subjects receiving either glucose or water. In addition, the decrease in blood glucose was markedly lower for the subjects receiving the present supplement.

Figure 7:
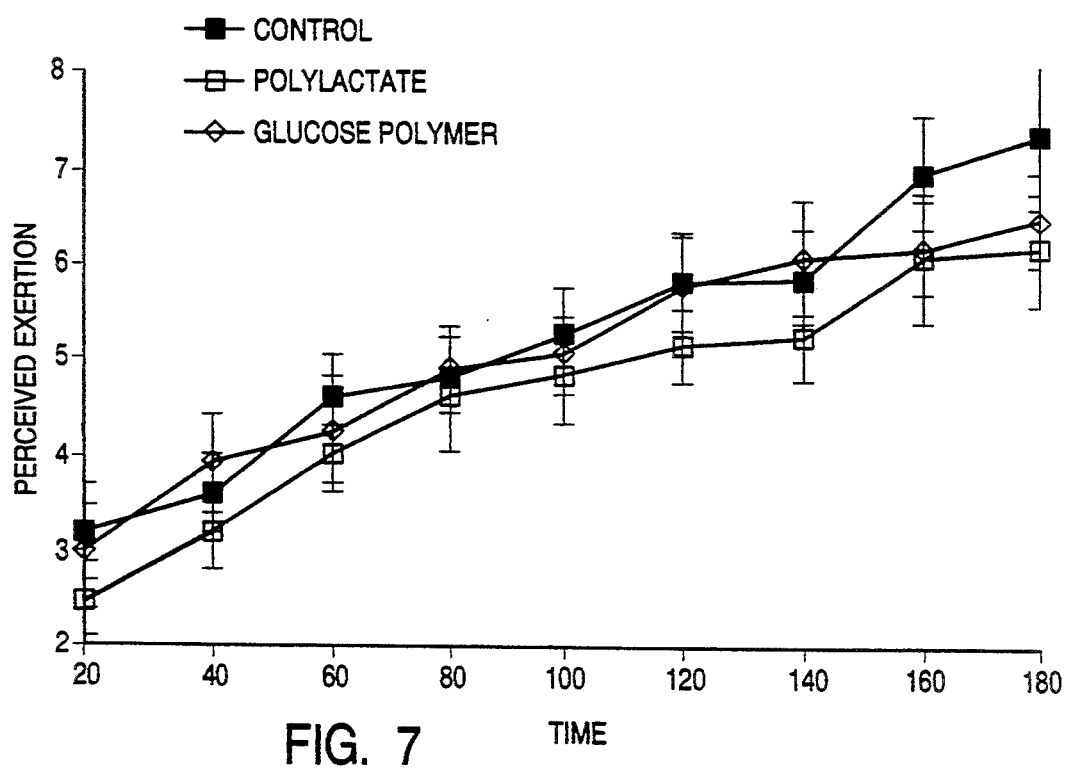
FIG. 7 is a graphic comparison of the exertion perceived by subjects receiving a supplement according to the invention with subjects receiving carbohydrate or water during sustained exercise.

As shown in FIG. 7, the perceived exertion levels reported by the subjects tended to be higher for control (7.3±0.8) and glucose (6.4±0.5) recipients than for subjects receiving the present supplement (6.1±0.7).

Figure 3:
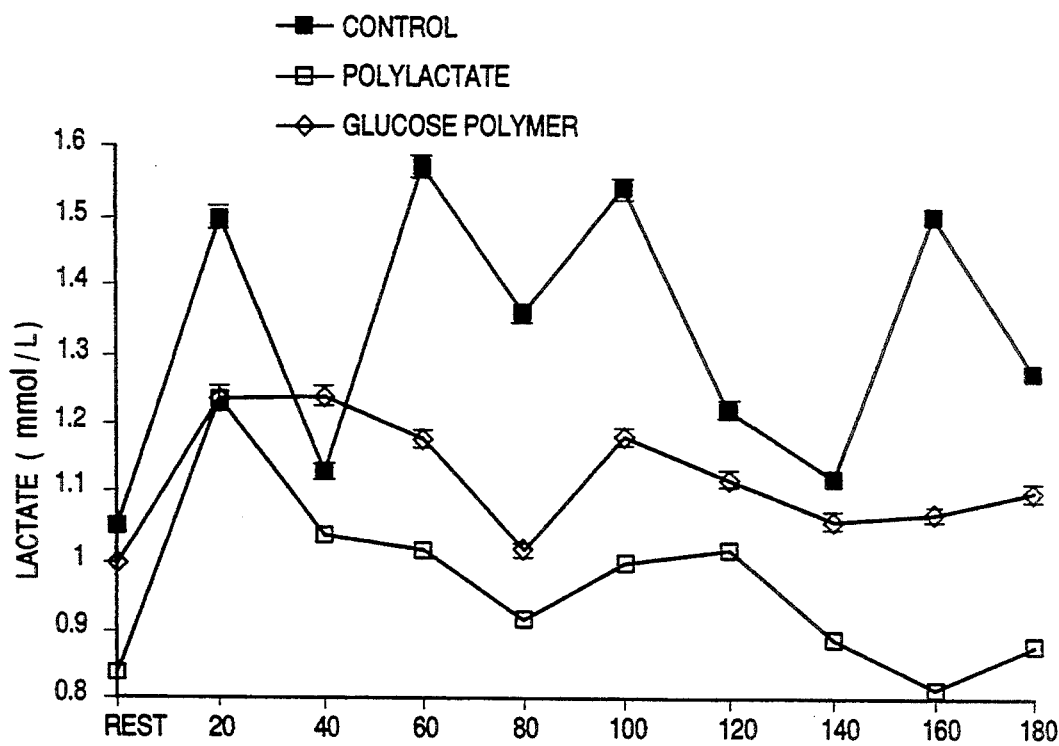
FIG. 3 is a graphic comparison of the venous blood lactate of subjects receiving a supplement according to the invention with subjects receiving carbohydrate or water during sustained exercise.

No significant differences were found between the subjects for sodium, potassium, chloride, or lactate (FIG. 3) concentrations, weight loss, heart rate, oxygen consumption, rectal temperature, or selected skin temperatures.

These data demonstrate that the present nutritional supplement can help maintain blood glucose levels and enhance blood buffering capacity during prolonged exercise and provides a useful athletic fluid replacement beverage.

Although the foregoing invention has been described in some detail by way of illustration for purposes of clarity of understanding, it will be obvious to those skilled in the art that numerous changes and modifications may be practiced within the spirit and scope of the appended claims.

I claim:

1. A method of enhancing the energy supply of an athlete during exercise and exercise recovery, said method comprising the steps of:
   preparing an aqueous fluid replacement solution comprising from about 1 to about 10% w/v of a combination consisting of about 10-20% an inorganic salt of lactic acid and about 90-80% L-arginyl-l(+)-lactate; and
   administering said solution to said athlete.

2. The method of claim 1, wherein the inorganic lactic acid salt is selected from the group consisting of ammonium lactate, calcium lactate, potassium lactate, sodium lactate and magnesium lactate.

3. The method of claim 1, wherein the L-arginyl-l(+)-lactate is a polymer.

4. The method of claim 3, wherein the L-arginyl-l(+)-lactate polymer has the following general structure:

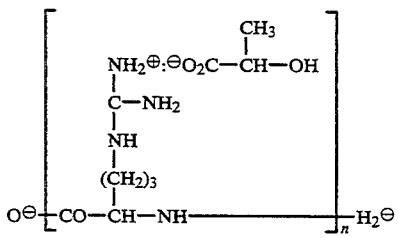

where n>1.

5. The method of claim 1, wherein the aqueous solution additionally comprises simple or complex carbohydrates.

6. The method of claim 5, wherein the simple carbohydrate is glucose or fructose.

7. The method of claim 5, wherein the complex carbohydrate is selected from the group consisting of glucose polymers from five to ten monomeric units.

8. A fluid replacement solution comprising:
   an aqueous solution consisting of:
   a) from about 10-20% of an inorganic lactic acid salt; and
   b) from about 90-80% of a lactate formed from L(+)-lactate anion and at least one member selected from the group consisting of cations of L isomeric forms of basic amino acids;
   wherein the total amount of said inorganic lactic acid salt and said lactate is from about 1 to about 10% w/v of said aqeuous solution.

9. The solution of claim 8 wherein the inorganic lactic acid salt is selected from the group consisting of ammonium lactate, calcium lactate, potassium lactate, sodium lactate and magnesium lactate.

10. The solution of claim 8, wherein the basic amino acid is selected from the group consisting of L-Arginine, L-Histidine and L-Lysine.

11. The solution of claim 10, wherein the lactate is L-Arginyl-L(+)-lactate.

12. The solution of claim 8 wherein said lactate is a polymer.

13. The solution of claim 12 wherein said polymer comprises poly(L-Arginyl-L(+)-lactate) having the following general structure:

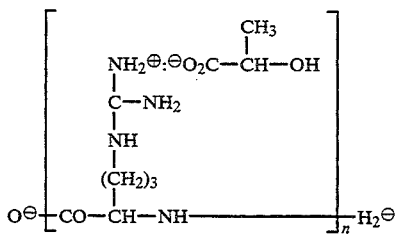

where n>1.

14. The said aqueous solution further comprises simple or complex carbohydrates.

15. The solution of claim 14, wherein the simple carbohydrate is glucose or fructose.

16. The solution of claim 14, wherein the complex carbohydrate is at least one member selected from the group consisting of glucose polymers of from five to ten monomeric units.

17. The solution of claim 14, wherein the simple or complex carbohydrate components are in accordance with the following dosages:
   Mono- and Disaccharide simple carbohydrates in a final concentration of from approximately 0.4 to 2.0 weight percent; and
   Polysaccharide complex carbohydrates in a final concentration of from approximately 0.8 to 4.0 weight percent.

18. An aqueous solution useful for enhancing the energy supply of an athlete during exercise and exercise recovery, said aqueous solution including about 7% w/v of a combination consisting of 80% polyarginyl lactate and 20% sodium lactate.

* * * * *

UNITED STATES PATENT AND TRADEMARK OFFICE
CERTIFICATE OF CORRECTION

PATENT NO. : 5,420,107
DATED : May 30, 1995
INVENTOR(S) : George A. Brooks

It is certified that error appears in the above-indentified patent and that said Letters Patent is hereby corrected as shown below:

Column 4, line 5, $CHO^3H^5O_3^{\ominus}$, should read "$C_3H_5O_3^{\oplus}$".

Signed and Sealed this

Fifth Day of September, 1995

Attest:

BRUCE LEHMAN

Attesting Officer

Commissioner of Patents and Trademarks